(12) United States Patent
Rutten et al.

(10) Patent No.: US 7,904,179 B2
(45) Date of Patent: Mar. 8, 2011

(54) IMPLANTABLE MEDICAL DEVICE SYSTEM WITH FIXATION MEMBER

(75) Inventors: Jean J. G. Rutten, Bocholtz (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 137 days.

(21) Appl. No.: 12/038,949

(22) Filed: Feb. 28, 2008

(65) Prior Publication Data

US 2008/0208339 A1 Aug. 28, 2008

Related U.S. Application Data

(60) Provisional application No. 60/892,048, filed on Feb. 28, 2007.

(51) Int. Cl.
*A61N 1/05* (2006.01)

(52) U.S. Cl. .......................................... 607/128

(58) Field of Classification Search .................. 607/116, 607/119, 128; 128/848
See application file for complete search history.

(56) References Cited

U.S. PATENT DOCUMENTS

| 3,754,555 | A | 8/1973 | Schmitt |
| 3,814,104 | A | 6/1974 | Irnich et al. |
| 3,835,864 | A | 9/1974 | Rasor et al. |
| 3,902,501 | A | 9/1975 | Citron et al. |
| 3,976,082 | A | 8/1976 | Schmitt |
| 4,144,890 | A | 3/1979 | Hess |
| 4,233,992 | A | 11/1980 | Bisping |
| 4,257,428 | A | 3/1981 | Barton et al. |
| 4,258,724 | A * | 3/1981 | Balat et al. ..................... 607/128 |
| 4,280,512 | A | 7/1981 | Karr et al. |
| 4,378,023 | A | 3/1983 | Trabucco |
| 4,419,819 | A | 12/1983 | Dickhudt et al. |
| 4,475,560 | A * | 10/1984 | Tarjan et al. .................. 607/128 |
| 4,607,644 | A | 8/1986 | Pohndorf |
| 4,721,118 | A | 1/1988 | Harris |
| 4,832,687 | A | 5/1989 | Smith, III |
| 4,858,623 | A | 8/1989 | Bradshaw et al. |
| 4,913,164 | A | 4/1990 | Greene et al. |
| 4,957,118 | A | 9/1990 | Erlebacher |
| 5,078,407 | A | 1/1992 | Calston et al. |
| 5,203,348 | A * | 4/1993 | Dahl et al. .................... 607/129 |
| 5,238,007 | A | 8/1993 | Giele et al. |
| 5,248,302 | A * | 9/1993 | Patrick et al. ................. 604/178 |
| 5,300,106 | A * | 4/1994 | Dahl et al. .................... 607/119 |
| 5,344,439 | A | 9/1994 | Otten |
| 5,514,174 | A | 5/1996 | Heil, Jr. et al. |
| 5,571,162 | A | 11/1996 | Lin |
| 5,637,097 | A * | 6/1997 | Yoon ............................. 604/174 |
| 5,667,520 | A | 9/1997 | Bonutti |
| 5,766,248 | A | 6/1998 | Donovan |

(Continued)

FOREIGN PATENT DOCUMENTS

WO WO03018130 A2 3/2003

(Continued)

*Primary Examiner* — Niketa I Patel
*Assistant Examiner* — Hiba El-Kaissi
(74) *Attorney, Agent, or Firm* — Stephen W. Bauer; Reed A. Duthler

(57) ABSTRACT

A fixation device for a subcutaneous implantable medical device includes a deformable tip portion that reduces in width when coupled with a fixation tool such that implantation of the implantable medical device through tissue is facilitated. Upon release from the fixation tool, the fixation device returns to its initial shape and stably secures the position of the implantable medical device.

10 Claims, 12 Drawing Sheets

U.S. PATENT DOCUMENTS

| | | |
|---|---|---|
| 5,782,841 A | 7/1998 | Ritz et al. |
| 5,944,732 A | 8/1999 | Raulerson et al. |
| 6,161,047 A | 12/2000 | King et al. |
| 6,200,237 B1 | 3/2001 | Barrie |
| 6,605,094 B1 | 8/2003 | Mann et al. |
| 6,999,819 B2 | 2/2006 | Swoyer et al. |
| 2003/0199961 A1 | 10/2003 | Bjorklund et al. |
| 2004/0204734 A1 | 10/2004 | Wagner et al. |
| 2004/0210293 A1 | 10/2004 | Bardy et al. |
| 2004/0230279 A1 | 11/2004 | Cates et al. |
| 2006/0030885 A1* | 2/2006 | Hyde .................. 606/232 |
| 2006/0122676 A1 | 6/2006 | Ko et al. |
| 2006/0247753 A1 | 11/2006 | Wenger et al. |

FOREIGN PATENT DOCUMENTS

| | | |
|---|---|---|
| WO | WO2005099805 | 10/2005 |

* cited by examiner

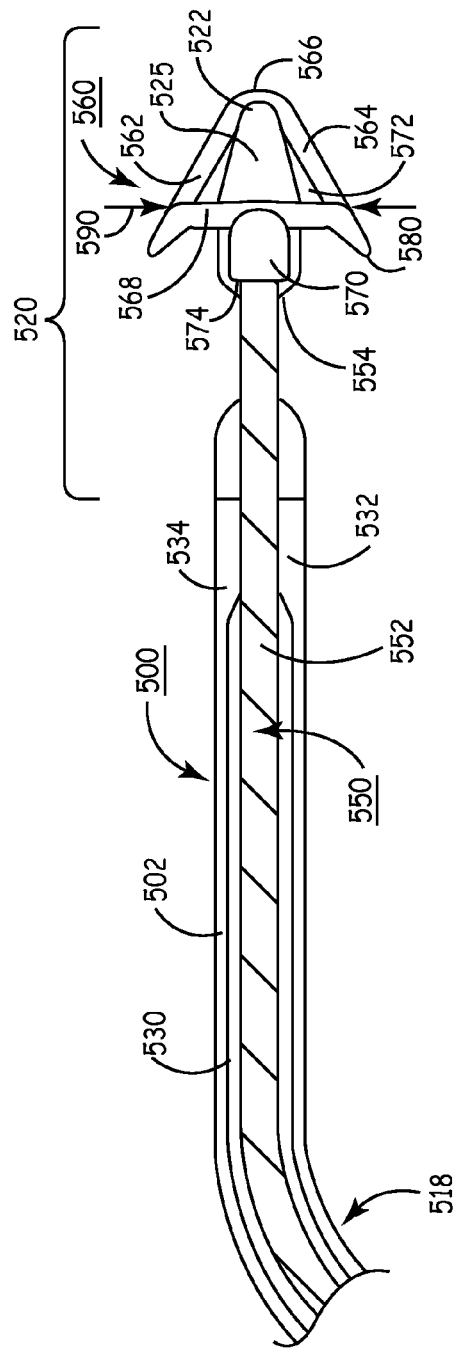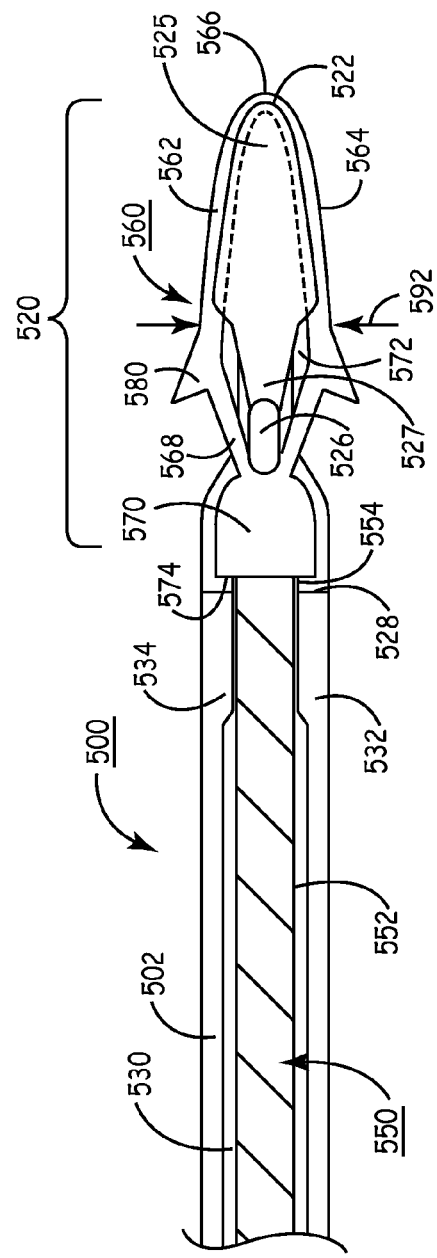

IMPLANTABLE MEDICAL DEVICE SYSTEM WITH FIXATION MEMBER

RELATED APPLICATIONS

This application is related to, and claims the benefit of, provisionally-filed U.S. Patent Application Ser. No. 60/892, 048, filed Feb. 28, 2007, and entitled "Implantable Medical Device System with Fixation Member", which is incorporated herein by reference in its entirety.

TECHNICAL FIELD

The invention relates generally to implantable medical devices and, in particular, to a fixation member for an implantable medical device.

BACKGROUND

Implantable medical devices are often provided with a fixation member for maintaining the device at a desired location within a patient's body. For example, elongated medical devices such as catheters and electrical leads may include a fixation member at or near the distal end of the device for maintaining the position of the device at a targeted implant site. Fixation members can include active and/or passive fixation members, for example in the form of hooks, barbs, helices or tines.

Implantable medical leads are used for deploying electrodes or physiological sensors to a targeted implant site. The lead carries electrical conductors allowing electrical connection of the deployed electrodes or sensors to a medical device such as a pacemaker, implantable cardioverter defibrillator, neurostimulator, or physiological monitor. Fluid delivery catheters may be used for delivering a fluid to a targeted body site to achieve an optimal effect. Fluid delivery catheters are generally coupled to a pump or other fluid dispensing device. A fluid delivered to a targeted site may be a dye used in a monitoring or diagnostic procedure, or a pharmaceutical agent or genetic or biological material for achieving a therapeutic effect. Reliable monitoring and/or therapy delivery by an implanted medical device is typically dependent on proper and stable positioning of the medical device. As such, many medical devices require a fixation member that reliably maintains the position of the device at a targeted body site without causing significant tissue trauma. In some cases, a delivery tool is needed for deploying the device to the targeted site.

Depending upon the nature of the medical device, fixation may be permanent or temporary. Thus, the fixation mechanisms is selected accordingly. For example, a cardiac pacing/ defibrillation lead is implanted for long term use and the fixation mechanism may be rather robust, such as a helical member screwed into tissue. Conversely, many catheters are inserted on a temporary basis. Thus, while important to secure these device in place as needed; it is also important to be able to remove and retract these devices from the human body without adverse consequence.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein:

FIGS. 15 and 16 are top plan views of a medical device including a fixation member being mounted on the delivery tool shown in FIGS. 13 and 14.

DETAILED DESCRIPTION

Figure 1:
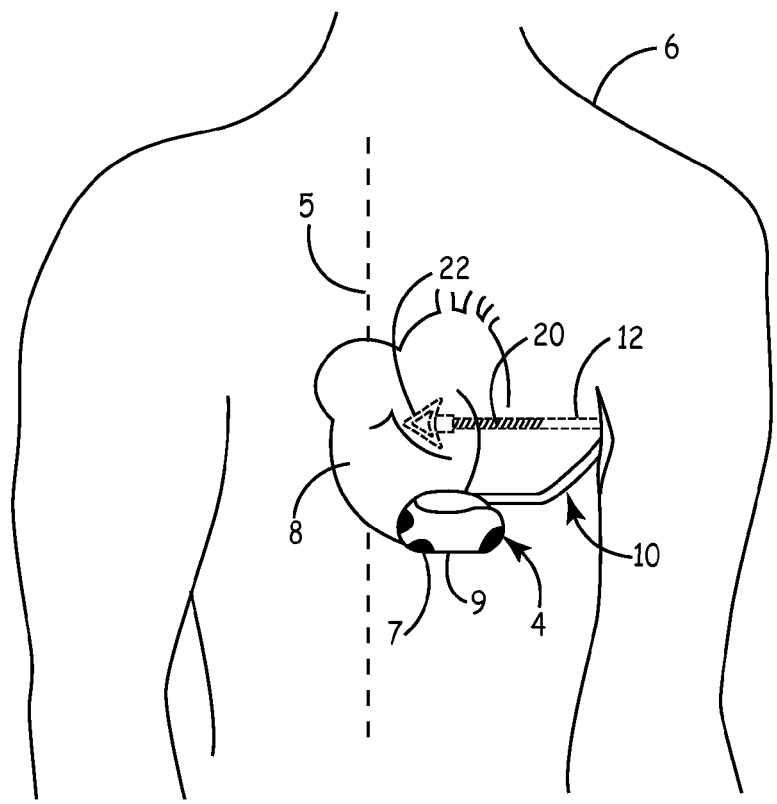
FIG. 1 depicts a patient implanted with a subcutaneous implantable cardioverter defibrillator.

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, drawings referred to herein are not shown to scale.

Embodiments of the invention include implantable medical device systems wherein an implantable medical device is provided with a fixation member for maintaining a stable implant position. Such systems will typically include an elongated medical device, such as an electrical lead or a fluid delivery catheter, that is tunneled or advanced to a targeted implant site for monitoring physiological signals and/or delivering a therapy. Embodiments of a medical device system include a delivery tool used to deploy the elongated medical device to the target site. Exemplary applications of various embodiments include implantable pacemaker systems, implantable cardioverter defibrillator systems, implantable neurostimulator systems, implantable drug delivery systems, implantable physiological monitoring systems or any other implantable medical device system relying on stable fixation of a medical device at an implant site. Implant sites may be subcutaneous sites, sub- or intramuscular sites, within the brain cavity, thoracic cavity, pleural cavity, within an organ wall, within a lumen of a vessel or organ, or any other internal body site.

FIG. 1 depicts a patient 6 implanted with a subcutaneous implantable cardioverter defibrillator (SubQ ICD) 4. SubQ ICD 4 is coupled to an implantable medical lead 10. Lead 10 includes an elongated lead body 12 including a coil electrode 20 and lead 10 is adapted for subcutaneous implantation. Lead 10 includes a fixation member 22 for maintaining the position of coil electrode 20 at a desired body site. In FIG. 1, SubQ ICD 4 is implanted in an anterior position relative to the patient's heart 8. The housing 9 of SubQ ICD 4 is used in conjunction with subcutaneous coil electrode 20 for delivering high-voltage shocks to the patient's heart. SubQ ICD 4 includes electrodes 7 that are used for sensing electrical signals from the heart such as, for example, to detect ventricular arrhythmias that need to be shocked. Lead body 12 is passed through a subcutaneous tunnel disposed laterally along the patient's chest wall, toward the patient's spine 5 to position coil electrode 20 posteriorly, relative to the heart 8. Fixation member 22 maintains the position of coil electrode 20 in the posterior position such that appropriate shocking vectors can be established between SubQ ICD 4 and coil electrode 20 relative to heart 8 to enable successful cardioversion/defibrillation of heart 8. SubQ ICD 4 and associated lead 10 illustrate one implantable medical device system in which embodiments of the present invention may be implemented.

Figure 2:
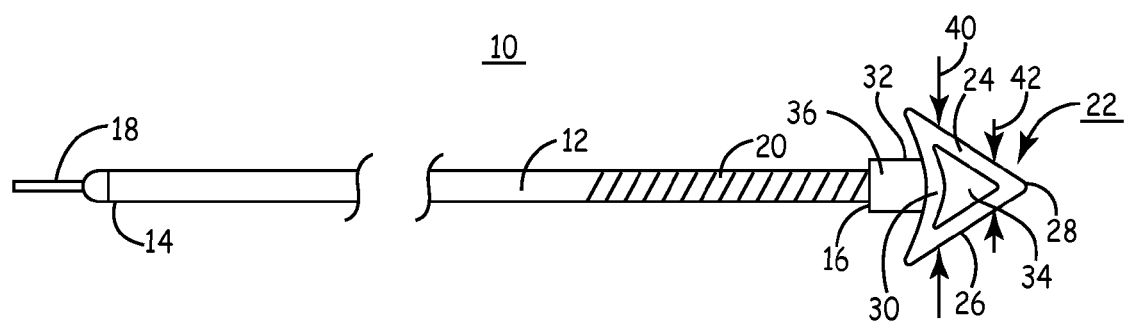
FIG. 2 is a plan view of the lead shown in FIG. 1.

FIG. 2 is a plan view of the lead 10 shown in FIG. 1. Lead 10 includes elongated lead body 12 extending between a proximal end 14 and a distal end 16. Lead body 12 is typically fabricated from a flexible insulative material including one or more lumens for carrying conductors (not shown) extending between proximal end 14 and distal end 16. A connector assembly 18 at proximal end 14 facilitates electrical connection of lead 10 to an associated medical device, such as SubQ ICD 4 shown in FIG. 1. One or more electrodes and/or physiological sensors are positioned along lead body 12, at or near distal lead body end 16. In the embodiment shown in FIG. 2, a coil electrode 20 used in delivering high energy shock pulses for cardioverting or defibrillating the heart is positioned along lead body 12 near distal end 16.

In other embodiments, lead 10 may be adapted for use with other implantable medical devices such as pacemakers, neurostimulators, physiological monitors or the like. As such, it is recognized that lead 10 may be adapted for carrying additional electrodes and/or other physiological sensors. Lead 10 may include additional coil electrodes, and/or lead 10 may include one or more ring electrodes used for sensing and/or stimulation. Other sensors carried by lead 10 may include temperature sensors, motion sensors, pressure sensors, electrodes for measuring impedance, oxygen sensors, etc.

A fixation member 22 is coupled to the lead body distal end 16 for maintaining a stable position of lead body distal end 16 upon deployment of lead 10 to an implant site. Fixation member 22 includes a first side 24 and a second side 26. First side 24 and second side 26 converge to form a distal tip 28. A proximal base 30 extends between first side 24 and second side 26 along a proximal end 32 of fixation member 22. Fixation member 22 is generally tapered such that the distance 40 between first side 24 and second side 26 near base 30 is greater than the distance 42 between first side 24 and second side 26 near distal tip 28. Fixation member 22 is shown to be generally triangular in shape having substantially straight first and second sides 24 and 26, which converge to form distal tip 28.

First side 24 and second side 26 form an aperture 34 therebetween for receiving a delivery tool used for tunneling and advancing lead 10 to a targeted implant site. Fixation member 22 further includes a receptacle 36 for receiving lead body distal end 16 to enable fixation member 22 to be coupled to lead body distal end 16.

Figure 3:
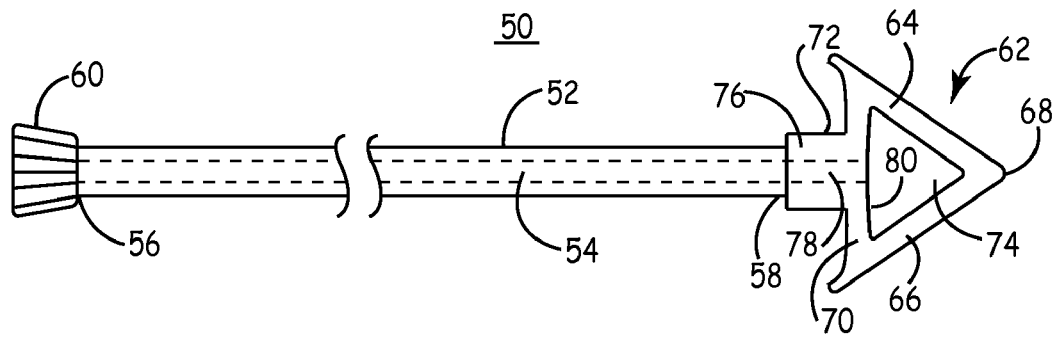
FIG. 3 is a plan view of a fluid delivery device including a fixation member.

FIG. 3 is a plan view of a fluid delivery device including a fixation member. Fluid delivery device 50 is embodied as a catheter including an elongated body 52 forming a lumen 54 extending between a proximal end 56 and distal end 58 of body 52. A fitting 60 is provided at proximal end 56 to enable coupling of device 50 to a fluid pump, syringe or other fluid dispensing device. Fixation member 62 is provided at catheter body distal end 58 for maintaining the position of distal end 58 at a desired body site.

Fixation member 62 includes a first side 64 and a second side 66, which converge to form a distal tip 68, forming an aperture 74 therebetween for receiving a delivery tool adapted for advancing fluid delivery device 50 to a desired body site. Fixation member 62 is shown to be generally triangular in shape and includes a proximal base 70 extending between first side 64 and second side 66 at fixation member proximal end 72. Fixation member 62 further includes a receptacle 76 for receiving catheter body distal end 58 to facilitate coupling of fixation member 62 to catheter body 52. Receptacle 76 may include a lumen 78 in communication with lumen 54 of catheter body 52 and a port 80 adapted to dispense a fluid flowing through lumens 54 and 78 to a targeted body site. Other apertures or ports may be provided along catheter body 52 in fluid communication with lumen 54 for dispensing a fluid. Fluid delivery device 50 may be used for delivering dyes, pharmaceutical solutions, or biological or genetic material.

Although not shown, it is recognized that fluid delivery device 50 may include electrodes or other sensors positioned along catheter body 52 and coupled to insulated conductors extending within catheter body 52. Likewise, it is recognized that the lead 10 shown in FIG. 2 could include a delivery lumen in communication with delivery port for delivering fluids or other medical devices.

Figure 4A:
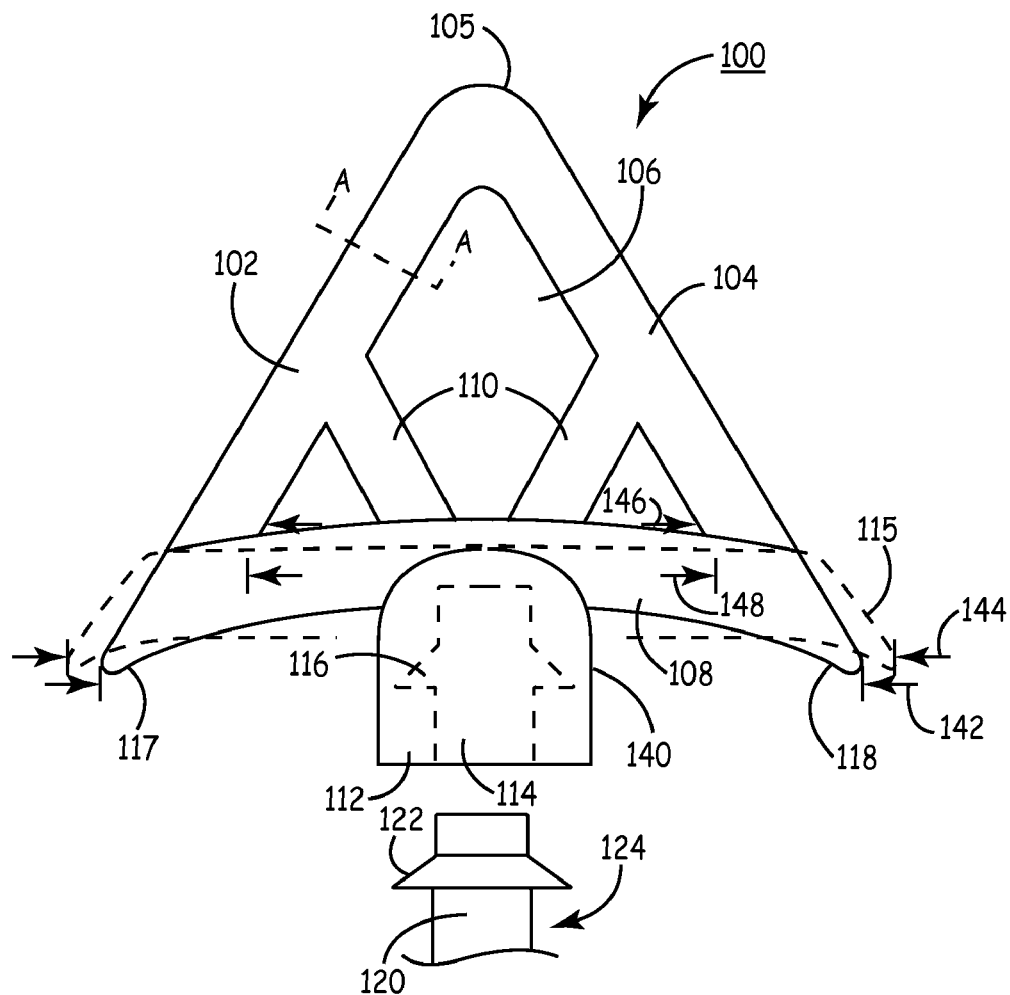
FIGS. 4A through 4C are plan views of various embodiments of a fixation member for use with an implantable medical device.

FIG. 4A is a plan view of a fixation member 100 for use with an implantable medical device. Fixation member 100 is coupled to the distal end 120 of an elongated medical device 124 to provide stable fixation of the medical device distal end 120 at a desired body location. Receptacle 112 of fixation member 100 includes a bore 114 adapted to receive distal medical device end 120. In one embodiment, distal end 120 is press fit within bore 114 and may be secured with an adhesive, such as silicone medical adhesive, to fixedly attach distal end 120 within receptacle 112. In other embodiments, bore 114 and medical device distal end 120 are provided with interlocking members or other features for providing a stable mechanical coupling of bore 114 with medical device distal end 120. In the embodiment shown in FIG. 4A, bore 114 includes a groove 116 adapted to mate with a flange 122 extending radially from medical device distal end 120. Flange 122 and groove 116 are adapted to allow medical device distal end 120 to be advanced into bore 114 until flange 122 and groove 116 interlock and thereafter act to retain medical device distal end 120 within receptacle 112. Coupling between receptacle 112 and medical device distal end 120 may be further stabilized by using an adhesive, such as a silicone medical adhesive. It is recognized that other interlocking or mating structures may be provided to promote a stable mechanical junction between fixation member 100 and medical device distal end 120. In alternative embodiments, fixation member 100 may be molded onto medical device distal end 120.

Fixation member 100 is formed from a resilient, biostable, polymeric material, such as a medical grade silicone rubber. In one embodiment, fixation member is molded from silicone rubber having a 70 durometer Shore A hardness. Appropriate silicone rubber materials are available from NuSil Technology, Carpinteria, Calif. As will be further described below, fixation member 100 is mounted on a delivery tool which is used to advance fixation member 100 to a desired body site. Fixation member 100 is configured to withstand tunneling forces required during an implant procedure and stretching that may be applied to mount fixation member on the delivery tool. Fixation member 100 is further configured to have a bending flexibility that allows it to wrap around and narrowly conform to the delivery tool during advancement to an implant site. However, the bending flexibility is balanced with a stiffness and resiliency needed to cause fixation member 100 to resume its previous shape upon release from the delivery tool and to retain that shape during body movement. Various aspects of fixation member 100 that allow member 100 to be designed with a desired tensile strength, stiffness and bending flexibility for optimal performance will be further described herein.

Fixation member 100 includes a delivery tool aperture 106 formed by first side 102 and second side 104. Distal tip 105 is shown to be a generally rounded, atraumatic tip. However, it is recognized that in alternative embodiments, tip 105 may be provided as a sharper or pointed tip to facilitate tunneling through tissue to an implant site. In some embodiments tip 105 may be formed having a greater stiffness to withstand tunneling forces. Once positioned at a targeted site, the width of fixation member 100 along proximal base 108 inhibits retraction or dislodgement of fixation member 100 away from the target site.

Base 108 may be provided with barbs 117 and 118 extending in a generally proximal direction to inhibit retraction of fixation member 100 from a desired implant site. Barbs 117 and 118 also inhibit retraction or dislodgement of fixation member 100 and act to prevent curling or flexing of fixation member, thereby maintaining fixation member in a generally flat configuration.

Base 108 is shown as an arcuate segment, curving slightly inward toward distal tip 105. Body motion, such as movement associated with respiration or activity, may cause tugging on elongated body 120. Proximal tension applied to fixation member 100, e.g. tugging on elongated body 120 that may occur with body motion, will initially cause the proximal end 140 of fixation member to widen from a normal width 142 to an extended width 144. Widening of proximal end 140 is caused by the straightening of arcuate base 108, as indicated by dashed line 115, and the resultant outward flexing of barbs 117 and 118 as proximal tension is applied by elongated body 120. A distance 146 between first side 102 and second side 104 in a relaxed state initially increases to a greater distance 148 in response to proximal tension. This initial widening of fixation member 100 in response to applied tension inhibits retraction or dislodgement of member 100 from the implant site.

Application of greater proximal tension causes fixation member 100 to elongate and narrow. As such, if retraction of fixation member 100 is required, greater proximal tension may be used to retract fixation member 100. In one embodiment, fixation member 100 is designed to withstand a retraction force of approximately 2 Newtons prior to becoming dislodged from a subcutaneous implant location.

Fixation member 100 includes support beams 110 extending between first side 102 and base 108 and between second side 104 and base 108. Support beams 110 serve to support first and second sides 102 and 104 and base 108 in a generally flat profile after implantation, i.e. beams 110 act to reduce bending or flexing of fixation member 100 after implantation.

Figure 4B:
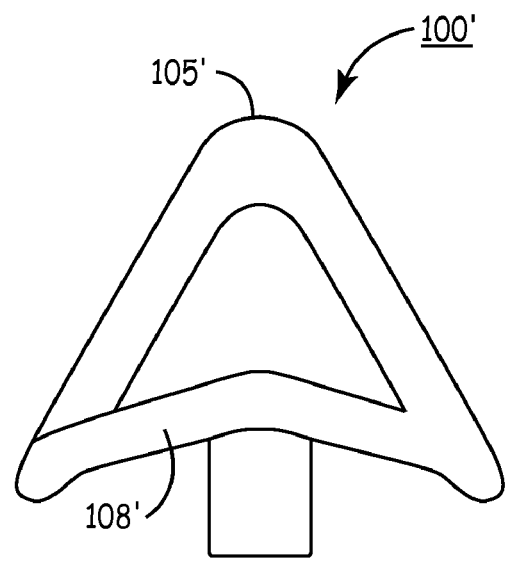

It is recognized that a fixation member may be provided with alternative base configurations in various embodiments of the invention. In FIG. 4B, a base 108' of fixation member 100' is shown having an inverted "V" shape. Base 108' extends inward toward distal tip 105'. In this configuration, proximal tension applied to base 108' will cause initial widening of fixation member 100' as base 108' is straightened in response to the proximal tension.

Figure 4C:
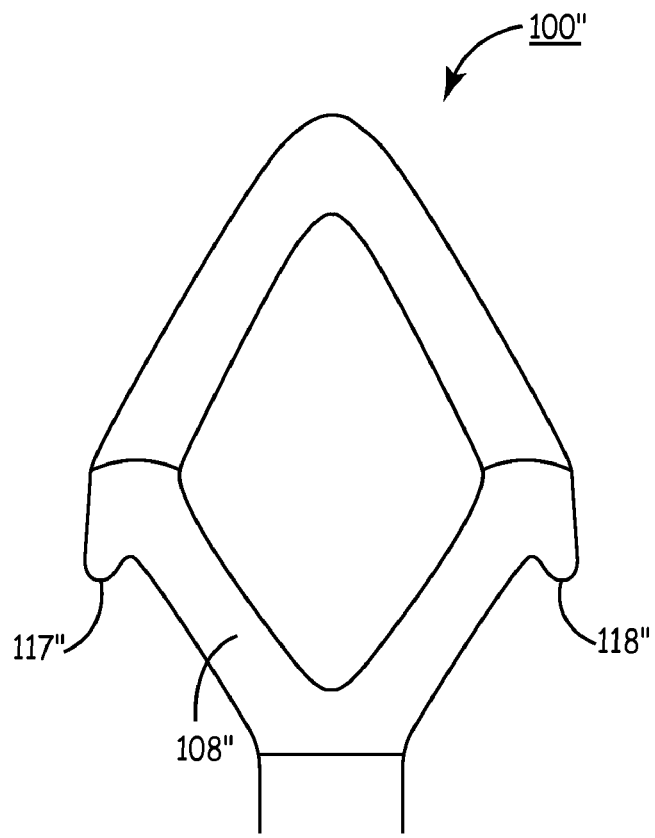

In FIG. 4C, a base 108" of fixation member 100" is shown having a "V" shape. Proximal tension applied to base 108" will cause narrowing of fixation member 100" as it is stretched over a delivery tool for advancement to an implant site. Barbs 117" and 118" may be provided which flex slightly outward in response to proximal tension causing an initial widening of fixation member 100".

Figure 5A:
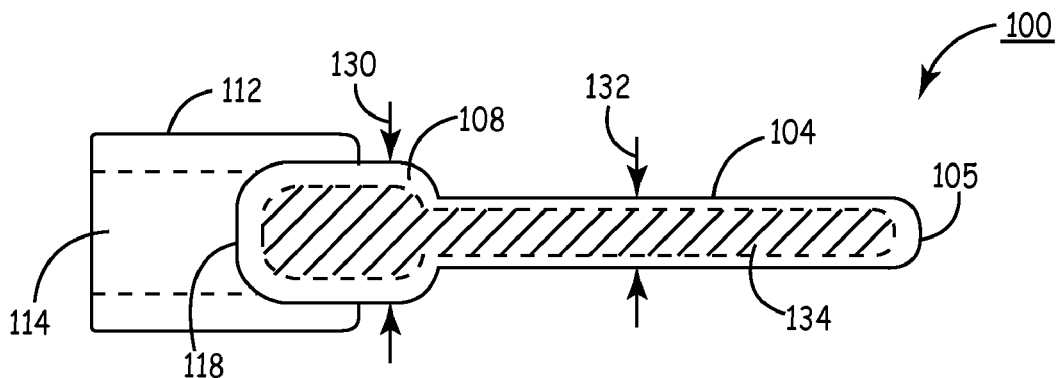
FIG. 5A is a side view of the fixation member shown in FIG. 4A.

FIG. 5A is a side view of fixation member 100 shown in FIG. 4A. Fixation member 100 has a generally flat profile. As described above, fixation member 100 includes first side 102 (not visible in the side view of FIG. 5), second side 104, distal tip 105, proximal base 108 having barb 118 and a receptacle 112 forming a bore 114 for receiving a medical device distal end. The flat profile allows stable fixation of a medical device in a subcutaneous position while minimizing patient discomfort. To reduce bending or flexing of first side 102, second side 104 and base 108 after implantation, base 108 is provided with a greater thickness 130 than the thickness 132 of sides 102 and 104. A greater stiffness of base 108, corresponding to its greater thickness, helps to maintain the flat, generally triangular shape of fixation member 100. As will be described in greater detail below, the greater stiffness of base 108 also supports expansion of fixation member from a stretched and rolled or wrapped configuration when mounted on a delivery tool to an expanded, generally flat configuration upon release from the delivery tool. Relatively thinner sides 102 and 104 facilitate easier mounting and releasing from the delivery tool and allow for an overall smaller size of fixation member 100 and an associated delivery tool. A smaller sized fixation member and smaller delivery tool will generally cause less tissue trauma. The thickness and stiffness of base 108 relative to sides 102 and 104 may be designed according to a particular application for achieving desired tensile strength and bending stiffness of fixation member 100.

Fixation member 100 is shown having material 134 coupled along side 104. Material 134 is provided to promote tissue adhesions to further promote stable fixation of member 100. Material 134 may be provided as a mesh or porous material that encourages tissue ingrowth. In one embodiment, material 134 is provided as polyethylene terephthalate fiber material (Dacron®, available from DuPont).

Figure 5B:
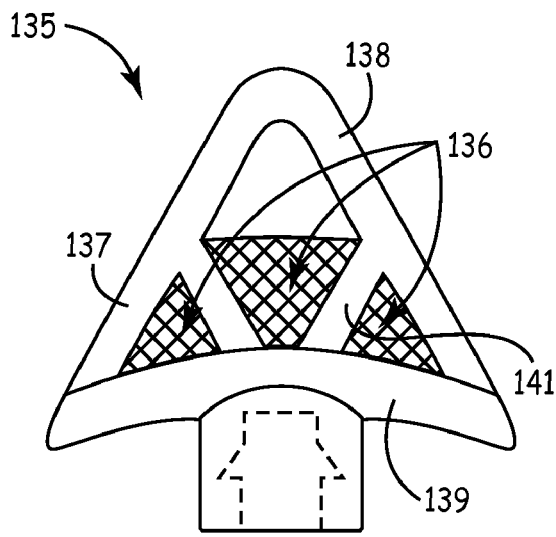
FIG. 5B is a plan view of a fixation member including material for promoting tissue ingrowth.

FIG. 5B is a plan view of a fixation member including additional material for promoting tissue ingrowth. In addition to, or alternatively to, providing a material covering a portion of the fixation member for promoting tissue adhesion, material 136 may be provided extending between any of first side 137, second side 138, base 139 and/or support beams 141 of a fixation member 135. Material 136 increases the stiffness of fixation member 135 which will improve the stable fixation of member 135 at an implant site acutely. By promoting tissue ingrowth, material 136 improves chronic stability of the fixation member at the implant site.

Figure 6A:
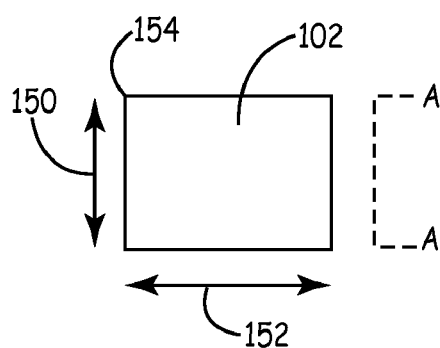
FIG. 6A is a cross-sectional view of a fixation member side.
Figure 6B:
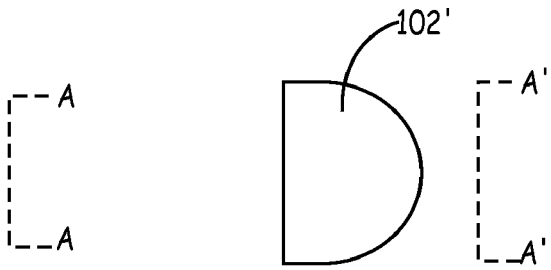
FIG. 6B is a cross-sectional view of a fixation member side in an alternative embodiment.

FIG. 6A is a cross-section of fixation member first side 102 along view A-A shown in FIG. 4A. The cross-sectional shape of sides 102 and 104 and base 108 may be generally quadrilateral as shown, for example, in FIG. 6A. In particular, side 102 is shown having a rectangular cross-section with squared corners 154. Squared corners 154 are expected to reduce slippage of fixation member 100 after implantation in comparison to rounded corners. Moreover, providing first and second sides 102 and 104 with a quadrilateral cross-section allows fixation member 100 to be designed with a desired balance between tensile strength and bending stiffness. The balance between tensile strength and bending stiffness is controlled by adjusting the thickness 150 and the width 152 of side 102 (and second side 104 and base 108). A rectangular cross-section allows better control over the balance of tensile strength and flexibility than a circular cross-section. For example the flexibility of side 102 can be increased by reducing thickness 150 while the tensile strength can be increased by increasing width 152. However, it is recognized that the cross-sectional shape of sides 102 and 104 as well as base 108 may include one or more rounded corners. For example, side 102' is shown to be generally D-shaped in FIG. 6B. In still other embodiments, sides 102 and 104 and base 108 may be generally circular or oval in cross-section.

Figure 7:
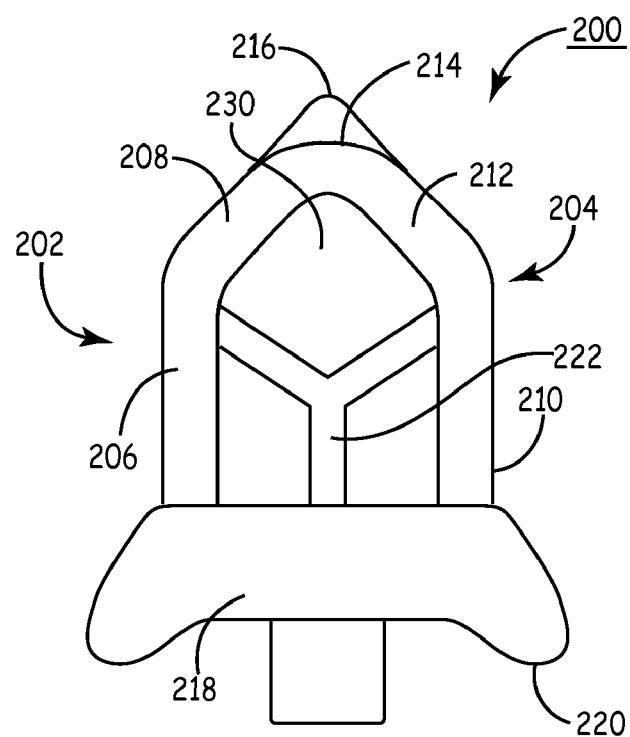
FIGS. 7 and 8 are plan views of alternative embodiments of a fixation member for use with a medical device.

It is contemplated that numerous configurations for a fixation member having first and second sides converging to form a distal tip and forming a delivery tool aperture there between may be conceived. In alternative embodiments the first and second sides may include curved (concave or convex) and parallel segments, or any combination of thereof. For example, as shown in FIG. 7, fixation member 200 includes sides 202 and 204 each having generally straight, parallel segments 206 and 210, respectively, and generally curved segments 208 and 212, respectively. Curved segments 208 and 212 converge to form distal tip 214.

In some embodiments distal tip 214 may include a rigid plastic or metal material. Distal tip 214 is shown in FIG. 7 having a rigid pointed cap 216 for facilitating tunneling of fixation member 200 to an implant site. Rigid cap 216 may be formed of a relatively stiffer silicone rubber, a rigid polymer, or a metal. In some embodiments, a rigid material is coupled to first and second sides 202 and 204 as they converge to form a rigid distal tip.

Support beams extending between the first and second sides and the proximal base may also be provided in a variety of configurations. In FIG. 7, a "Y" shaped support beam 222 extends between each of sides 202 and 204 and base 218. An aperture 230 is formed by sides 202 and 204 and support beam 222 for receiving a delivery tool.

The shape and size of barbs provided on the proximal base may also vary. Base 218 is provided with rounded barbs 220 extending in a generally proximal direction.

Figure 8:
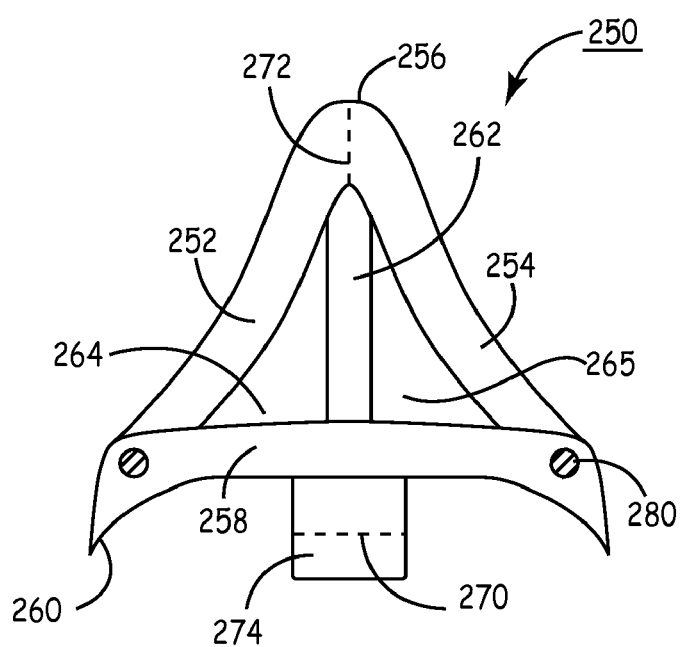

In FIG. 8, fixation member 250 includes convex first and second sides 252 and 254 which converge to form distal tip 256. A support beam 262 extends between distal tip 256 and base 258. Base 258 includes pointed barbs 260 extending in a generally proximal direction for inhibiting retraction of fixation member 250. Apertures 264 and 265 are formed by support beam 262 and side 252 and side 254, respectively. One or both apertures 264 and 265 may be adapted to receive a delivery tool.

Fixation member 250 may be provided as a splittable member having one or more break points indicated by lines 272 and 270. Fixation member 250 is designed to have a tensile strength that withstands the pushing forces needed to tunnel fixation member 250 to a desired implant site when mounted on a delivery tool. In some situations, retraction of the medical device and fixation member 250 is required. In order to facilitate retraction of fixation member 250, fixation member 250 is provided with a relatively weaker break point 272 or 270. Upon applying a retraction force exceeding the tensile strength of fixation member 250 across the break point 272 or 270, fixation member 250 will split along the break point 270 or 272. A break point 272 provided along distal tip 256, or along either side 252 and 254, will allow fixation member 250 to split, then elongate and collapse inward as it is retracted through a tissue tunnel.

Alternatively, a break point 270 may be provided along receptacle 274, at a point distal to the coupling between fixation member 256 and a medical device. Break point 270 would allow the receptacle 274 to split from the remaining portion of fixation member 250. Upon retraction of the medical device, fixation member 250 would be left behind at the implant site. Fixation member 250 could then be removed from a subcutaneous position via a small incision if desired. Break points 270 and 272 may be formed, for example, as splittable seams, perforated lines, or as a narrowed outer diameter to create a weakened tensile strength across the break point relative to the remaining portions of fixation member 250.

In some embodiments, fixation member 250 is provided with radio-opaque markers 280 to allow visualization of fixation member 250 after implantation. Radio-opaque markers 280 may be used to verify the location of fixation member 250 during the implant procedure. If fixation member 250 is provide with a break point 272 along receptacle 274 and is left behind after retracting the associated medical device, radio-opaque markers 280 may be used to locate fixation member 250 for surgical removal.

Figure 9:
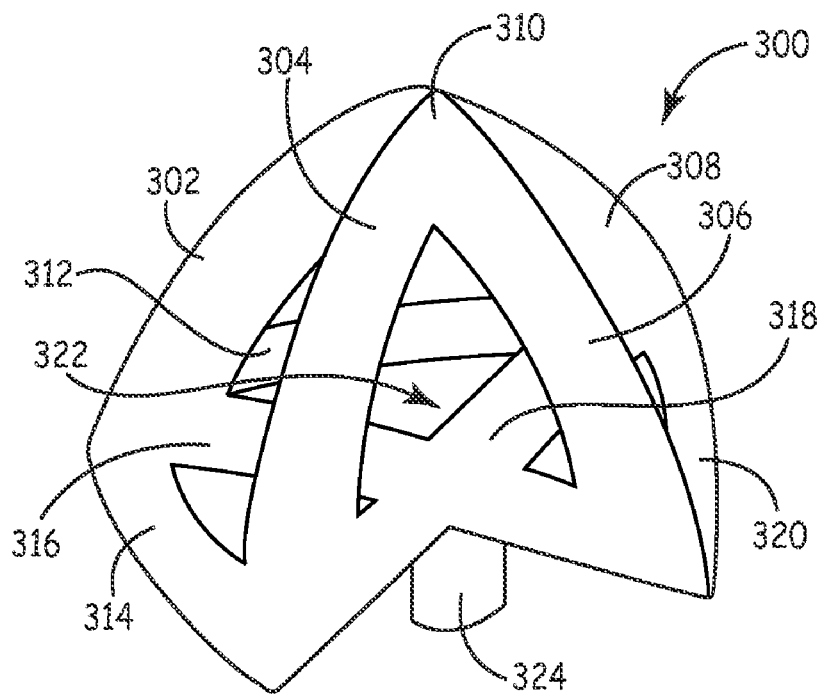
FIGS. 9 and 10 are perspective views of alternative embodiments of a fixation member.

Depending on the specific application, fixation member 100 may alternatively be formed having a more three-dimensional geometry rather than the substantially planar, low-profile geometries described above. FIG. 9 illustrates a fixation member 300 having a generally pyramidal shape, including multiple sides 302, 304, 306 and 308 converging to form distal tip 310. Fixation member 300 includes multiple base segments 312, 314, 316, 318 and 320 extending between respective pairs of sides 302, 304, 306 and 308. Sides 304 and 306 form an aperture 322 for receiving a delivery tool. Sides 304 and 306 are not joined by a base segment to allow more room for a delivery tool to be inserted into aperture 322. A receptacle 324 extends proximally from the intersection of base segments 316 and 318 for receiving a medical device distal end.

Figure 10:
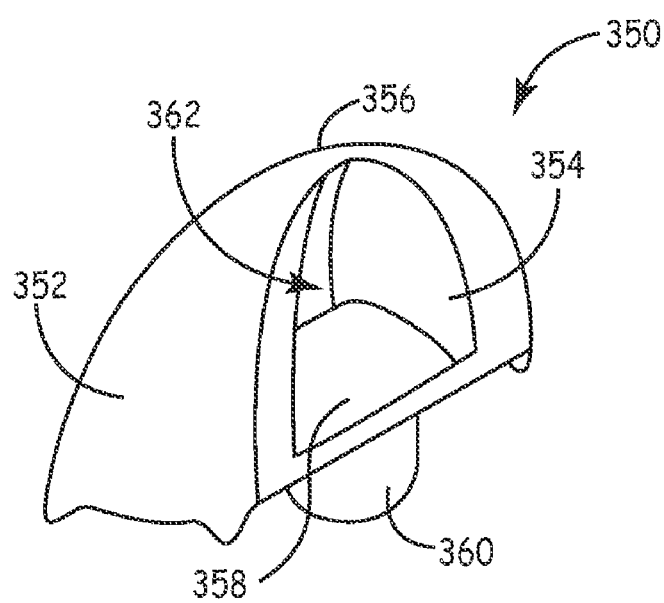

FIG. 10 is a perspective view of an alternative embodiment of a fixation member 350. Fixation member 350 is formed having first and second sides 352 and 354 which converge to from distal tip 356. Sides 352 and 354 form a portion of a hemisphere and are narrower near distal tip 356 and wider near proximal base 358. Sides 352 and 354 form an aperture 362 there between for receiving a delivery tool. A receptacle 360 extends proximally from base 358 for receiving a medical device distal end to allow coupling of fixation member 350 to the medical device. It is recognized that a variety of geometries for a fixation member may be conceived, including generally conical, pyramidal, or hemispherical shapes.

Figure 11:
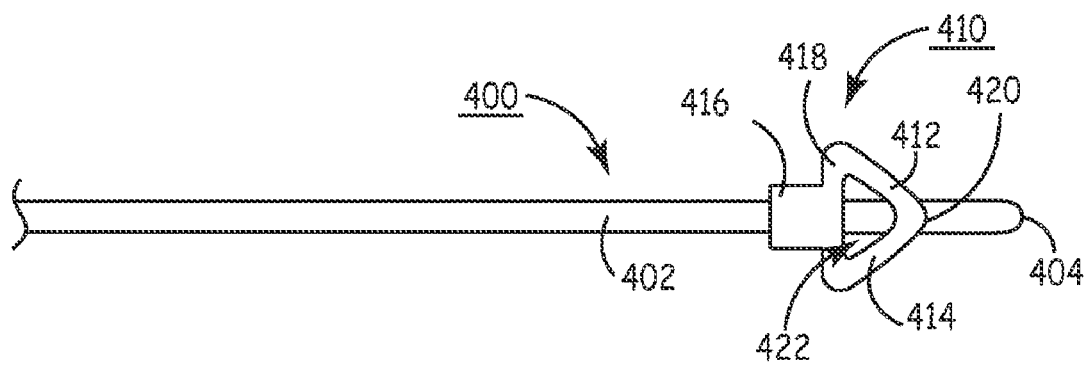
FIG. 11 is a top plan view of a medical device having a fixation member.

FIG. 11 is a top plan view of a medical device 400 having a fixation member 410. Fixation members provided according to various embodiments of the invention will generally be coupled to a distal end of an elongated medical device. However, according to an embodiment of the present invention, a fixation member 410 may be coupled at other points along an elongated body, or along other features of a medical device. For example, as illustrated in FIG. 11, a medical device 400 includes an elongated body 402 having a distal end 404. Fixation member 410 includes a first side 412 and second side 414, which converge to form a distal tip 420, and form a delivery tool aperture 422 there between. A proximal base 418 extends between first and second sides 412 and 414. A receptacle 416 extends proximally from base 418 and is coupled to medical device body 402 at a location proximal to distal end 404.

Figure 12:
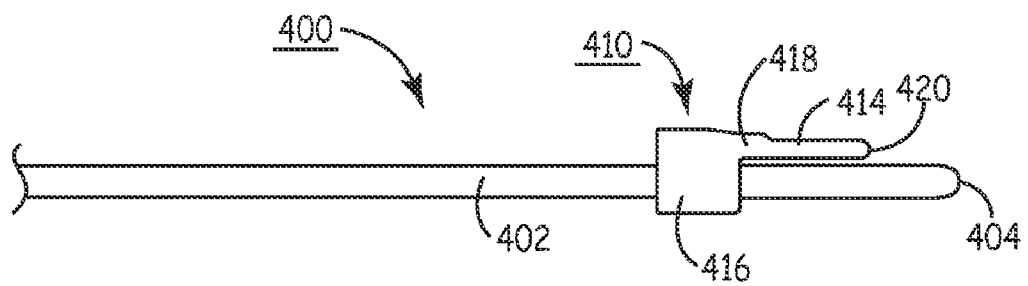
FIG. 12 is a side plan view of the medical device shown in FIG. 11.

FIG. 12 is a side plan view of the medical device 400 shown in FIG. 11 having fixation member 410. Receptacle 416 is offset from the plane of base 418 and second side 414 such that fixation member 410 can be coupled along elongated body 402, proximal to distal end 404. Fixation member 410 is offset from and extends substantially parallel to elongated body 402. It is recognized that fixation member 410 may alternatively be offset from and oriented at other angles with respect to elongated body 402.

Figure 13:
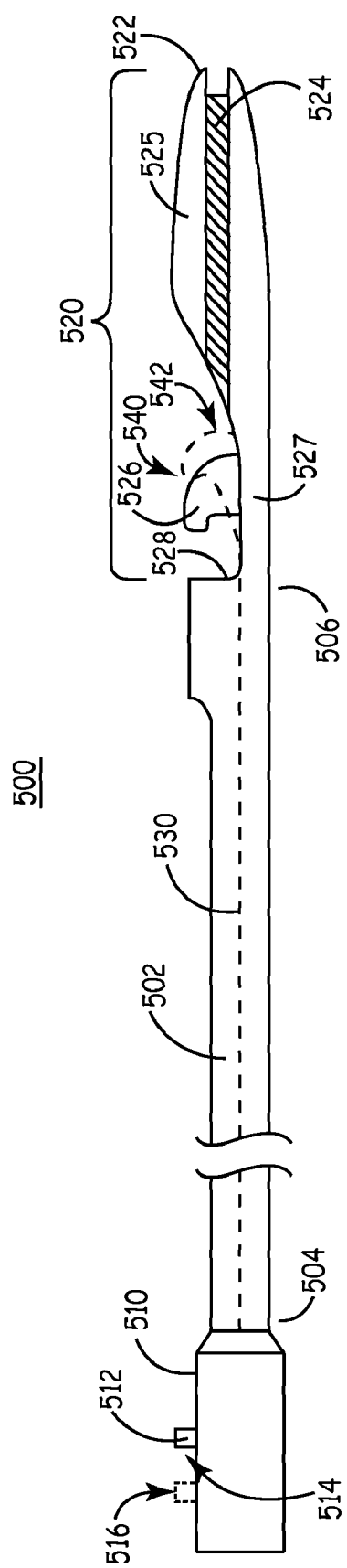
FIG. 13 is a side plan view and FIG. 14 is a top plan view of a medical device delivery tool.
Figure 14:
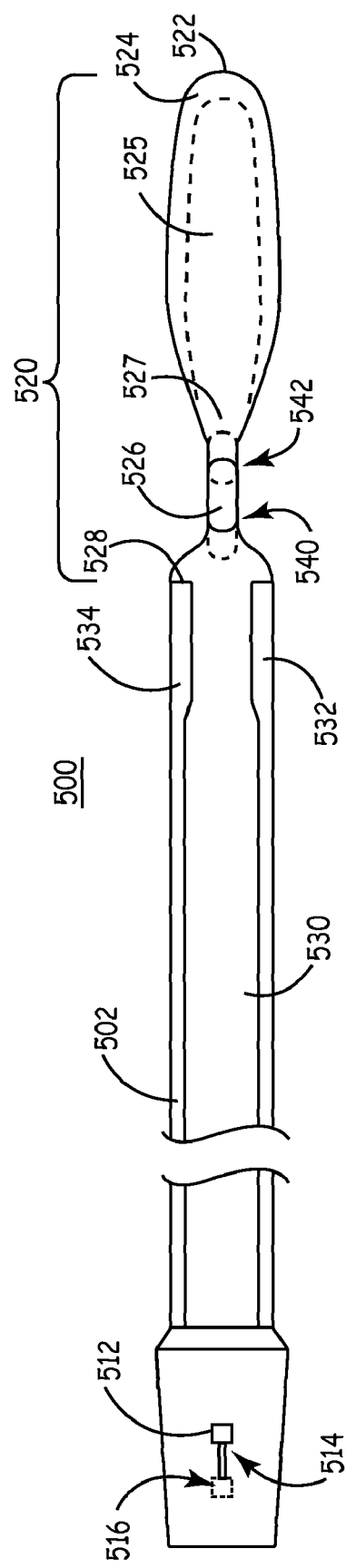

The various embodiments of a fixation member described herein include an aperture for receiving a delivery tool. FIG. 13 is a side plan view and FIG. 14 is a top plan view of a medical device delivery tool 500. Delivery tool 500 may be used for deploying a medical device having a fixation member as described above. Delivery tool 500 includes a shaft 502 which may be provided as a malleable shaft formed of stainless steel. Shaft 502 extends between a proximal end 504 and a distal end 506. A handle 510 is provided at proximal end 504 for maneuvering shaft 502 during an implant procedure. A delivery tool head 520 is provided at shaft distal end 506 for carrying a medical device during an implant procedure. In particular, delivery tool head 520 is adapted for carrying a fixation member coupled to an elongated medical device.

Delivery tool head 520 includes a distal tunneling tip 522 that is generally pointed for facilitating tunneling of tool 500 through body tissues to an implant site. Tunneling tip 522 may be rounded to reduce tissue trauma or more pointed to cut more easily through tissues thereby reducing the pushing force needed to advance delivery tool 500.

Delivery tool head 520 includes a mounting portion 525 for carrying a fixation member of a medical device. Mounting portion 525 is provided with a groove 524 extending along each side of mounting portion 525 and around tunneling tip 522. Groove 524 receives a medical device fixation member as will be further described below. Delivery tool head 520 includes a narrowed neck portion 527 extending proximally from mounting portion 525. Narrowed neck portion 527 allows a medical device fixation member to wrap around delivery tool head 520 such that the fixation member and head 520 become approximately isodiametric during advancement to an implant site.

Delivery tool head 520 further includes restraint 526 for retaining a portion of the medical device fixation member carried by tool head 520. Restraint 526 is designed to releasably hold a portion of the medical device fixation member. As will be further described below, a fixation member is stretched over mounting portion 525 with the fixation member proximal base held by restraint 526. Restraint 526 is designed to function as both a retaining and release mechanism. Proximal handle 510 includes a mechanical switch 512 for controlling restraint 526. In one embodiment, activation of switch 512 from a first position 514 (as shown) to a second position 516 (indicated by dashed line) actuates restraint 526 from a retaining position 540 (as shown) to a release position 542 (indicated by dashed line). Activation of switch 512 causes a rotation of restraint 526 via a pull wire (not shown). The rotation of restraint 526 pushes the fixation member proximal base up and away from delivery tool head 520. In alternative embodiments, delivery tool head 520 may include separate restraint and release mechanisms.

Switch 512 is a bistable switch in some embodiments in which a first stable position 514 corresponds to retaining a fixation member on delivery tool head 520 and a second stable position 516 corresponds to releasing the fixation member from the delivery tool head. Switch 512 may alternatively be provided as a monostable switch having a stable position corresponding to retaining the fixation member and provides tactile or audible feedback corresponding to the release of the fixation member from the delivery tool head. The circumferential position of switch 512 on handle 510 can also serve as an indicator of the orientation of delivery tool head 520.

Shaft 502 may be formed with a contoured outer surface, e.g. a concave surface 530, for accommodating an elongated body of the medical device. The length and cross-sectional contour of shaft 502 may vary depending on the particular application. Shaft 502 further includes one or more flanges 532 and 534 for maintaining the position of the elongated body along shaft 502 and inhibiting rotation or twisting of the elongated body of a medical device extending along shaft 502. Flanges 532 and 534 do not limit longitudinal movement (along the tool axis) of the elongated body relative to the shaft 502. As such, flanges 532 and 534 do not form a tight fit with the elongated body and provide a space therebetween so as to readily release the elongated body from tool 500 upon release of the fixation member from delivery tool head 520. However, it is contemplated that in some embodiments, flanges 532 and 534 may retain the elongated body for inhibiting longitudinal movement (along the tool axis) of the elongated body relative to shaft 502 as well as rotational movement. Shaft 502 further includes a stop surface 528 for interfacing with a surface of the medical device to prevent over-stretching of the fixation member carried by delivery tool head 520 as will be further described below.

FIGS. 15 and 16 are top plan views of a medical device 550 including a fixation member 560 being mounted on the delivery tool 500 shown in FIGS. 13 and 14. Delivery tool shaft 502 is shown in FIG. 15 having a pre-shaped curve or bend 518. Shaft 502 may be provided having one or more pre-shaped bends or curves to facilitate advancement of delivery tool 500 to an implant site. The particular configuration of shaft 502 may be selected according to the intended application.

In FIG. 15, fixation member 560 is shown in an unstretched, normal state. Fixation member 560 includes a first side 562 and a second side 564 which converge to form a distal tip 566. First side 562 and second side 564 form a delivery tool aperture 572 for receiving delivery tool head 520. Fixation member 560 includes proximal base 568 extending between first side 562 and second side 564. Base 568 is provided with barbs 580. A receptacle 570 extends proximally from base 568. A distal end 554 of medical device elongated body 552 is coupled to receptacle 570.

Delivery tool head 520 is inserted through fixation member aperture 572, and fixation member distal tip 566 is positioned in the groove 524 (shown in FIG. 13) of mounting portion 525. Medical device elongated body 552 extends along delivery tool shaft 502, resting along concave surface 530. Flanges 532 and 534 inhibit rotation or twisting of elongated body 552 relative to shaft 502.

In FIG. 16, fixation member 560 is shown in a stretched state, positioned on delivery tool head 520 for advancement to an implant site. Base 568 is stretched proximally by pulling medical device 550 back toward proximal end 504 of shaft 502 with distal tip 566 positioned within groove 524 of mounting portion 525 and held in the stretched position by restraint 526. In the stretched position, fixation member 560 becomes elongated and narrower to facilitate tunneling through tissue to an implant site. A distance 590 (FIG. 15) between first and second sides 562 and 564 along base 568 in relaxed state is reduced to a shorter distance 592 (FIG. 16) upon stretching fixation member 560 over delivery tool head 520. First and second sides 562 and 564 reside in groove 524 of mounting portion 525. Fixation member distal tip 566 and sides 562 and 564 protrude slightly from groove 524 of mounting portion 525. It is recognized that in some embodiments, fixation member distal tip 566 and first and second sides 562 and 564 may reside entirely within groove 524 of mounting portion 525. Groove 524 is sized to form a snug fit with fixation member 560 to prevent fixation member 560 from falling off delivery tool head 520 and to prevent tissue from becoming pinched between delivery tool head 520 and fixation member 560 during advancement to an implant site. Fixation member distal tip 566 and sides 562 and 564 are protected within groove 524 during advancement to a tissue site.

Fixation member 560, being stretched over delivery tool head, becomes narrower to facilitate tunneling to an implant site. Restraint 526 maintains the tension of fixation member 560 to keep member 560 from falling off the delivery tool head. In one embodiment, fixation member 560 is stretched to approximately 120% to 200% of its normal length when mounted on delivery tool head 520. In the stretched position, a proximal face 574 of receptacle 570 interfaces with stop surface 528 to prevent overstretching of fixation member 560. In some embodiments, restraint 526 is optional and stretching of fixation member 560 may be accomplished by an implanting clinician maintaining tension on the proximal end of the elongated medical device 550. The stop surface 528 prevents the clinician from overstretching fixation member 560.

Figure 17:
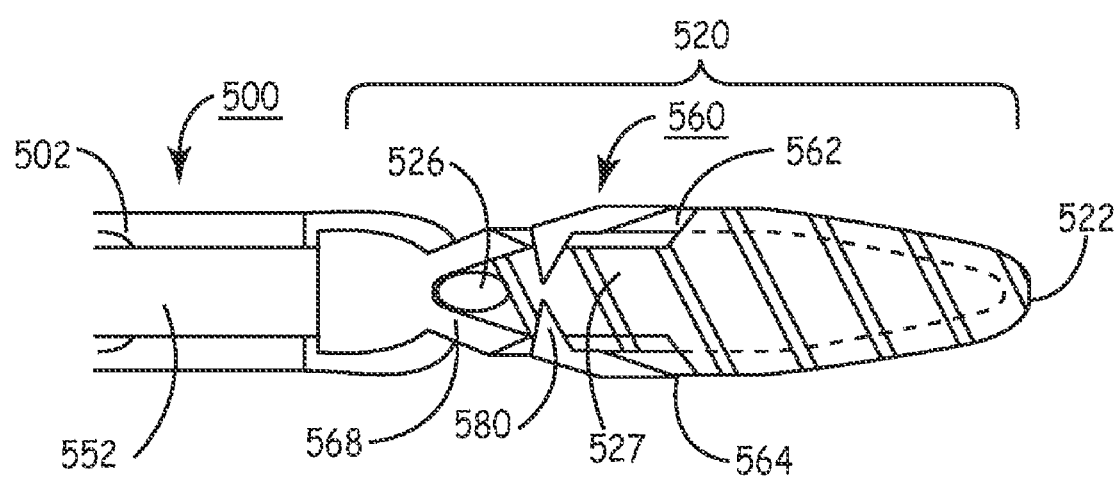
FIG. 17 is a top plan view of a distal portion of the fixation member mounted on the delivery tool shown in FIG. 16.

FIG. 17 is a top plan view of a distal portion of the fixation member 560 mounted on the delivery tool 500 shown in FIG. 16. As the tunneling tip 522 of delivery tool 500 is tunneled through tissue to a desired implant site, sides 562 and 564 of fixation member 560 fold in around narrowed neck portion 527 of delivery tool head 520. Fixation member 560 thus becomes substantially isodiametric with delivery tool head 520. As delivery tool head 520 and fixation member 560 are tunneled to an implant site a relatively narrow passage through the tissue is formed. A smaller diameter of the delivery tool head with a mounted fixation member will generally require lower tunneling forces. Upon release of fixation member 560 from delivery tool head 520, fixation member 520 regains its normal shape. As described previously, fixation member base 568 is formed with a greater stiffness than sides 562 and 564 such that base 568 will straighten upon release from tool 500 and thereby act to restore the generally triangular shape of fixation member 560. The wide base 568 of fixation member 560 and barbs 580 will inhibit the retraction of member 560 back through the narrow tissue tunnel formed by delivery device 500.

Figure 18:
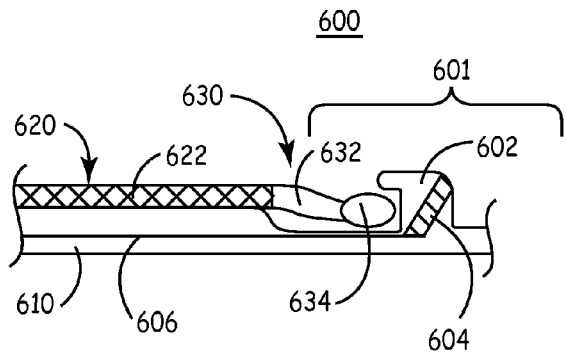
FIGS. 18 and 19 are side and top views, respectively, of a delivery tool distal portion having an alternative release mechanism used for releasing a fixation member from the delivery tool.
Figure 19:
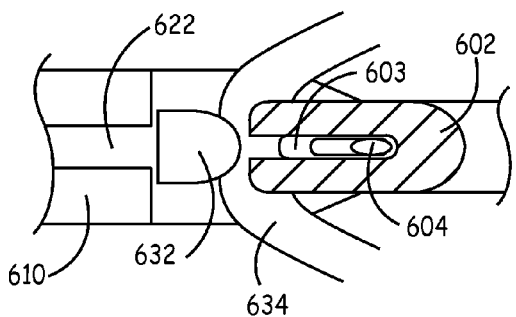

FIGS. 18 and 19 are side and top views, respectively, of a delivery tool distal portion having an alternative release mechanism used for releasing a fixation member from the delivery tool. A medical device 620 is shown mounted on delivery tool 600. Medical device 620 includes an elongated body 622 coupled to a receptacle 632 of fixation member 630. First and second sides of fixation member 630 are not shown for the sake of clarity in illustrating the release mechanism 604. Delivery tool 600 includes a shaft 610 and delivery tool head 601. Delivery tool head 601 includes a restraint 602 for retaining the base 634 of fixation member 630 in a stretched position.

Release mechanism 604 is embodied as a lever coupled to an actuation member 606, embodied as a push-pull rod. Actuation member 606 extends to a proximal handle of delivery tool 600 where it is attached to a mechanical switch (not shown) used to actuate release mechanism 604 via actuation member 606. Restraint 602 includes a groove 603 (FIG. 19) to allow longitudinal movement (along the tool axis) of release mechanism 604, toward and away from base 634.

Figure 20:
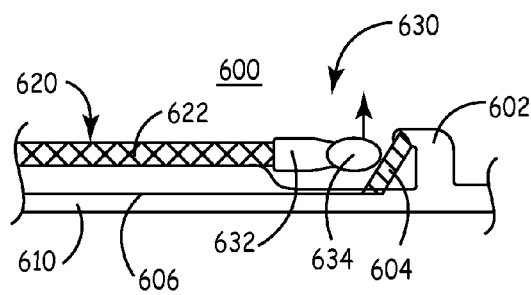
FIGS. 20 and 21 are side and top views, respectively, of the distal portion of the delivery tool shown in FIGS. 18 and 19 wherein the release mechanism has been actuated to release the fixation member from the delivery tool.
Figure 21:
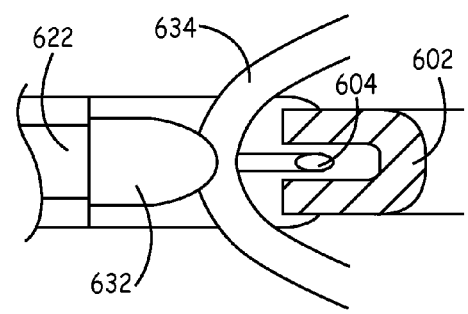

FIGS. 20 and 21 are side and top views, respectively, of the distal portion of the delivery tool 600 shown in FIGS. 18 and 19 wherein the release mechanism has been actuated to release fixation member 630 from delivery tool 600. Actuation of release mechanism 604 by a switch coupled to actuation member 606 causes release mechanism 604 to slide proximally toward base 634. Base 634 will be stretched slightly further by release mechanism 604 and pushed upward, as indicated by the arrow in FIG. 20, until base 634 is released from restraint 602. Fixation member 630 will then slip off delivery tool head 601 allowing tool head to be retracted and removed and leaving fixation member 630 at the implant site.

Figure 22:
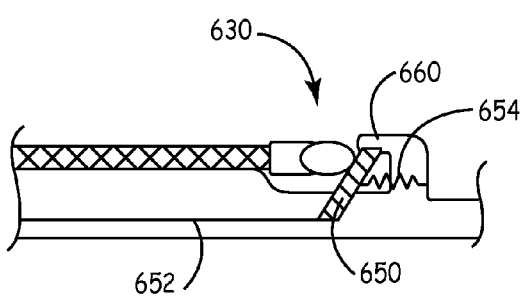
FIG. 22 is a side sectional view of an alternative embodiment of a delivery tool release mechanism.

FIG. 22 is a side sectional view of an alternative embodiment of a delivery tool release mechanism. An actuation member may alternatively be provided in the form of a pull wire 652 and spring member 654 instead of a push-pull rod as shown in FIGS. 18-21A. Tension applied to pull wire 652 by way of a proximal switch will pull release mechanism 650 proximally to release fixation member 630 from restraint 660. Spring member 654 will return release mechanism 650 back, distally, to its normal position corresponding to retaining a fixation member by restraint 660. Spring member 654 may be formed as a metal or polymer spring or an elastic element. In some embodiments, release member 650 may be designed having elastic properties that cause release member 650 to return to a normal position when not activated by pull wire 652.

While particular embodiments of release mechanisms have been shown and described herein, it is recognized that numerous delivery tool configurations may be conceived which enable restraint and release of a fixation member. Such arrangements may include a lever, spring, rod, or other member actuated by a mechanical switch for longitudinal or rotational movement that causes release of a medical device fixation member from the delivery tool. The particular details of such mechanisms may vary widely but such variations are considered within the scope of the present invention.

Figure 23:
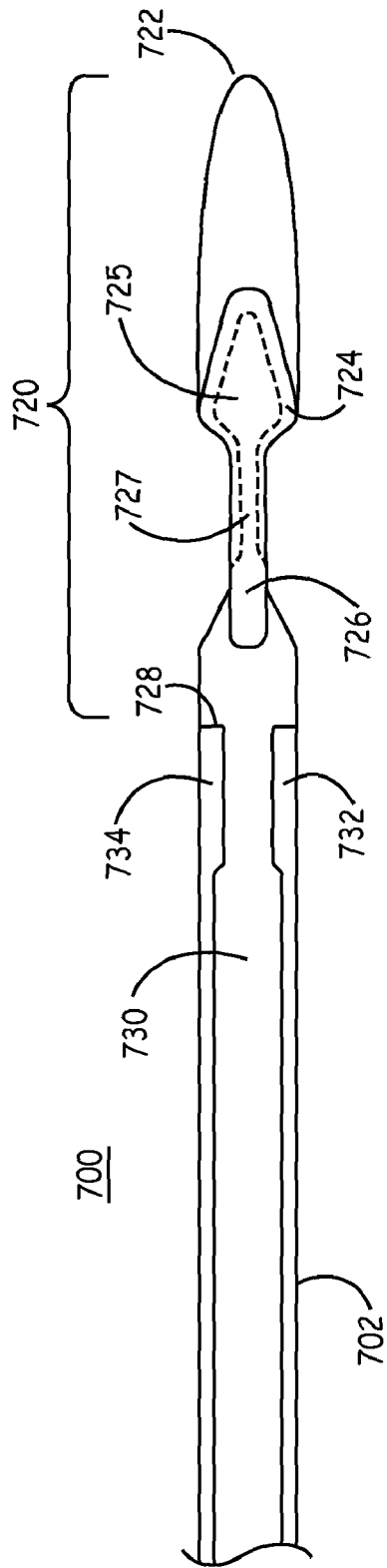
FIGS. 23 and 24 are side and top views, respectively, of an alternative embodiment of a delivery tool.
Figure 24:
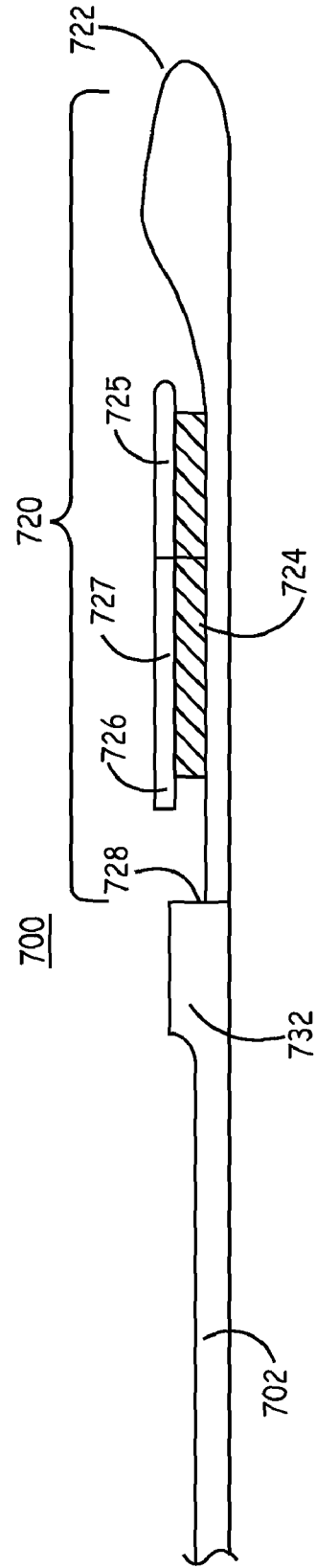

FIGS. 23 and 24 are side and top views, respectively, of an alternative embodiment of a delivery tool. Delivery tool 700 includes a mounting portion 725 positioned proximal to tunneling tip 722. Delivery tool 700 includes a shaft 702 having a contoured surface 730 for accommodating an elongated body of a medical device (not shown in FIGS. 23 and 24). Shaft 702 includes flanges 732 and 734 for inhibiting rotation and lateral movement of the medical device relative to shaft 702 and a stop surface 728 to prevent over-stretching of a fixation member mounted on delivery tool 700.

Delivery tool 700 further includes a delivery tool head 720 having a distal tunneling tip 722, a mounting portion 725 spaced proximally from tunneling tip 722 and a narrowed neck portion 727 extending toward shaft 702. A restraint 726 is provided for maintaining a fixation member in a stretched position when the fixation member is mounted along groove 724 of mounting portion 725 as described previously. A fixation member mounted on delivery tool head 720 is not exposed to the tunneling forces met by tunneling tip 722.

Thus, a medical device system including an implantable medical device having a fixation member and a delivery tool used for deploying the device have been presented in the foregoing description with reference to specific embodiments. It is appreciated that various modifications to the referenced embodiments may be made without departing from the scope of the invention as set forth in the following claims.

The invention claimed is:

1. An implantable medical device system, comprising:
a medical device;
a fixation member coupled to the medical device for maintaining the medical device at a targeted implant site; and
a delivery tool including a shaft extending between a proximal end and a distal end and a delivery tool head at the shaft distal end, wherein the fixation member is adapted to be releasably coupled to the delivery tool head, and
wherein the delivery tool head includes a mounting portion and wherein the fixation member is adapted to be stretched over the mounting portion when being coupled to the delivery tool head; and
wherein the delivery tool further includes a restraint for retaining the fixation member on the mounting portion in a stretched position.

2. The implantable medical device system of claim 1 wherein the delivery tool further includes a release mechanism for releasing the fixation member from the delivery tool head.

3. The implantable medical device system of claim 2 wherein the delivery tool further comprises a handle coupled to the proximal shaft end; and
a mechanical switch coupled to the handle, wherein the mechanical switch actuates the release mechanism.

4. The implantable medical device system of claim 2 wherein the release mechanism includes a pulling member extending along the shaft for actuating the release mechanism.

5. The implantable medical device system of claim 2 wherein the release mechanism further includes a spring member for returning the release mechanism to a normal position after releasing the fixation member.

6. The implantable medical device system of claim 3 wherein the mechanical switch is adapted to have a first stable position corresponding to retaining the fixation member by the restraint and a second stable position corresponding to releasing the fixation member from the restraint.

7. An implantable medical device system, comprising:
a medical device;
a fixation member having a selectively adjustable width coupled to the medical device for maintaining the medical device at a targeted implant site; and
a delivery tool including a shaft extending between a proximal end and a distal end and a delivery tool head at the shaft distal end wherein the fixation member is adapted to be releasably coupled to the delivery tool head, and
wherein the width of the fixation member is adjustable from a first width when the fixation member is coupled to the delivery tool to a second width when the fixation member is released from the delivery tool, and
wherein the fixation member includes a first side, a second side, a distal tip and a proximal base extending between the first side and the second side, wherein the first side and the second side converge to form the distal tip, the first side and the second side forming an aperture therebetween for receiving the delivery tool head; and
wherein the delivery tool head includes a narrowed neck portion and wherein the base is adapted to wrap around the narrowed neck portion to cause the fixation member to become approximately isodiametric with the delivery tool head.

8. An implantable medical device system, comprising:
a medical device;
a fixation member having a selectively adjustable width coupled to the medical device for maintaining the medical device at a targeted implant site; and
a delivery tool including a shaft extending between a proximal end and a distal end and a delivery tool head at the shaft distal end wherein the fixation member is adapted to be releasably coupled to the delivery tool head, and
wherein the width of the fixation member is adjustable from a first width when the fixation member is coupled to the delivery tool to a second width when the fixation member is released from the delivery tool, and
wherein the delivery tool shaft includes a stop surface, and the fixation member includes a proximal face interfacing with the stop surface and preventing overstretching of the fixation member when mounted on the delivery tool.

9. An implantable medical device system, comprising:
a medical device;
a fixation member having a selectively adjustable width coupled to the medical device for maintaining the medical device at a targeted implant site; and
a delivery tool including a shaft extending between a proximal end and a distal end and a delivery tool head at the shaft distal end wherein the fixation member is adapted to be releasably coupled to the delivery tool head, and
wherein the width of the fixation member is adjustable from a first width when the fixation member is coupled to the delivery tool to a second width when the fixation member is released from the delivery tool, and
wherein the medical device includes an elongated body and the delivery tool shaft includes a flange retaining the elongated body and limiting rotational movement of the device relative to the shaft.

10. An implantable medical device system, comprising:
a medical device;
a fixation member having a selectively adjustable width coupled to the medical device for maintaining the medical device at a targeted implant site; and
a delivery tool including a shaft extending between a proximal end and a distal end and a delivery tool head at the shaft distal end wherein the fixation member is adapted to be releasably coupled to the delivery tool head, and
wherein the width of the fixation member is adjustable from a first width when the fixation member is coupled to the delivery tool to a second width when the fixation member is released from the delivery tool, and
wherein the delivery tool shaft includes a contoured surface corresponding to and engaging an outer surface of the medical device and wherein the delivery tool head includes a mounting portion and wherein the fixation member is adapted to be stretched over the mounting portion when being coupled to the delivery tool head; and wherein the delivery tool further includes a restraint for retaining the fixation member on the mounting portion in a stretched position.

* * * * *